United States Patent

Günther et al.

[11] Patent Number: 4,683,308
[45] Date of Patent: Jul. 28, 1987

[54] PROCESS FOR THE PREPARATION OF 2-ARYLAMINO-4,6-DICHLORO-S-TRIAZINES

[75] Inventors: Andreas Günther, Cologne; James R. Malone, Dormagen; Manfred Lenthe, Odenthal; Hans-Walter Höhl, Cologne, all of Fed. Rep. of Germany

[73] Assignee: Bayer Aktiengesellschaft, Leverkusen, Fed. Rep. of Germany

[21] Appl. No.: 820,510

[22] Filed: Jan. 21, 1986

[30] Foreign Application Priority Data

Feb. 7, 1985 [DE] Fed. Rep. of Germany ....... 3504073

[51] Int. Cl.[4] ........................................... C07D 251/44
[52] U.S. Cl. .................................................. 544/211
[58] Field of Search ..................... 544/204, 208, 211

[56] References Cited

U.S. PATENT DOCUMENTS

| | | | |
|---|---|---|---|
| 2,720,480 | 10/1955 | Wolf | 167/33 |
| 2,820,032 | 1/1958 | Hill et al. | 260/249.5 |
| 3,074,946 | 1/1963 | Rattenburg et al. | 260/249.5 |
| 3,305,551 | 2/1967 | Picklesimer et al. | 544/208 |
| 3,310,557 | 3/1967 | Kleemann | 544/208 |
| 3,882,118 | 5/1975 | Narayan et al. | 544/208 |

FOREIGN PATENT DOCUMENTS 1670675 12/1970 Fed. Rep. of Germany .

Primary Examiner—John M. Ford
Attorney, Agent, or Firm—Sprung Horn Kramer & Woods

[57] ABSTRACT

In the preparation of a 2-arylamino-4,6-dichloro-s-triazine of the formula

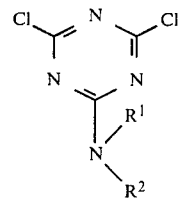

in which
$R^1$ is an optionally substituted aryl radical, and
$R^2$ is hydrogen or alkyl,
by reacting cyanuric chloride of the formula

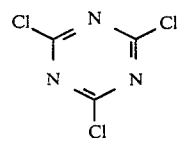

with a virtually water-insoluble arylamine of the formula

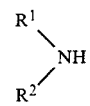

at a temperature between 0° and 100° C., the improvement which comprises effecting the reaction in water at an acid pH in the presence of a virtually water-insoluble organic solvent. The resulting aqueous phase contains the triazine in such high purity and concentration that it can be used without further purification. The organic solvent can be recycled.

8 Claims, No Drawings

PROCESS FOR THE PREPARATION OF 2-ARYLAMINO-4,6-DICHLORO-S-TRIAZINES

The present invention relates to an improved process for the preparation of known 2-arylamino-4,6-dichloro-s-triazines from cyanuric chloride and a virtually water-insoluble arylamine.

It is already known that 2-arylamino-4,6-dichloro-s-triazines are obtained when cyanuric chloride is reacted with arylamines in an aqueous medium. Various water-soluble auxiliaries have been added so that the reaction can be favorably influenced. Thus, for example, it is reported that acetone and sodium hydroxide are added (compare U.S. Patent Specification No. 2,720,480). It is furthermore known that the arylamines are employed in the form of water-soluble salts, for example as hydrochlorides (compare DE-OS (German Published Specification No.) 1,670,675), or that metal salts of ligninsulphonic acids are added (compare U.S. Patent Specification No. 2,820,032). The reaction proceeds relatively rapidly and with good yields.

These known processes in an aqueous medium have, however, a number of disadvantages. Thus, the purity of the product is only slightly above 90%, so that the products in general can be used only after further purification operations, such as recrystallization. Furthermore, the preparation is carried out in a relatively high dilution (less than 100 g of cyanuric chloride starting material per 1 of water), so that a poor space/time yield results. Finally, the auxiliaries employed can be removed from the process effluent only with difficulty, so that effluent problems arise.

It is moreover known that the reaction can also be carried out in an anhydrous medium in water-insoluble solvents, such as toluene (compare U.S. Patent Specification No. 3,074,946). However, long reaction times are required for this reaction, and in some cases poor, that is to say greatly varying, yields result. The object of the present invention is thus to provide an auxiliary which allows a higher purity of the product, less dilution of the reaction mixture and easy removal of the auxiliary from the process effluent, with the same high rate of reaction and high yield. It has been found that 2-arylamino-4,6-dichloro-s-triazines of the formula (I)

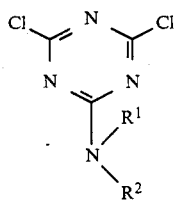

(I)

in which
R$^1$ represents an aryl radical which is optionally mono- or polysubstituted by identical or different substituents and
R$^2$ represents hydrogen or alkyl,
are obtained from cyanuric chloride of the formula (II)

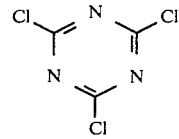

(II)

with a virtually water-insoluble arylamine of the formula (III)

(III)

in which R$^1$ and R$^2$ have the abovementioned meanings, at temperatures between 0° C. and 100° C., in a particularly advantageous manner, above all in a relatively high purity, by a process in that the reaction is carried out in water at an acid pH value in the presence of a virtually water-insoluble organic solvent.

It is to be described as decidedly surprising that in the reaction according to the invention of cyanuric chloride with a virtually water-insoluble arylamine in an aqueous medium, the reaction is favorably influenced in the presence of a virtually water-insoluble organic solvent, because in view of the prior art, it was not to be expected that a substance which is insoluble in the reaction medium would intervene advantageously in the reaction sequence, especially since it was known that it is also entirely possible to carry out the present reaction by itself in water-insoluble solvents (compare U.S. Patent Specification No. 3,074,946), long reaction times having been required with in some cases poor yields, that is to say greatly varying yields, as already described.

The process according to the invention has a number of advantages. Thus, a higher purity of the product is achieved with the same high rate of reaction and high yield. In addition, the space/time yield is increased by the reaction mixture being less dilute, and effluent problems are avoided by the easy removal of the auxiliary, that is to say the virtually water-insoluble organic solvent, from the process effluent.

If cyanuric chloride and o-chloroaniline are used as starting substances, the course of the reaction can be represented by the following equation:

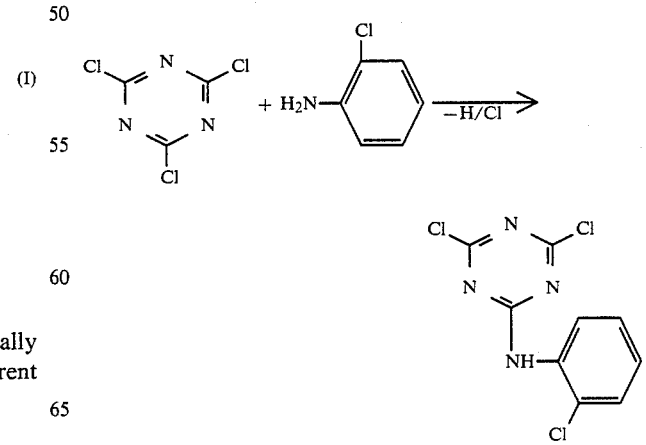

In formula (I), $R^1$ preferably represents a phenyl or naphthyl radical which is optionally mono-, di-, tri-, tetra- or pentasubstituted, in particular mono-, di- or trisubstituted, by identical or different substituents from the group comprising alkyl with 1 to 6, in particular 1 to 4, carbon atoms, such as methyl, ethyl, and isopropyl and n-, sec-, iso- and tert.-butyl, halogen, such as fluorine, chlorine, bromine and iodine, in particular chlorine, nitro, cyano, alkoxy with 1 to 5, in particular 1 to 3, carbon atoms and halogenoalkyl with 1 to 5, in particular to 3, carbon atoms and 1 to 5 identical or different halogen atoms, such as, for example, fluorine and chlorine, such as, for eXample, trifluoromethyl, dichlorofluoromethyl, chlorodifluoromethyl and 2-chloro-2-fluoroethyl, and $R^2$ preferably represents hydrogen or alkyl with 1 to 4, in particular 1 or 2, carbon atoms.

The cyanuric chloride of the formula (II) is well known and can be prepared on a large industrial scale, as is the case with the arylamines of the formula (III), for which the following examples may be mentioned: aniline, β-naphthylamine, α-naphthylamine, p-methylaniline, o-methylaniline, o-ethylaniline, 2,4-dimethylaniline, o-chloroaniline, m-chloroaniline, p-chloroaniline, p-bromoaniline, 2,5-dichloroaniline, 2,4-dichloroaniline, 2-methyl-3-chloroaniline, 4-nitroaniline, 2-chloro-4-nitroaniline, 4-cyanoaniline, 4-methoxyaniline, 2-methoxyaniline, p-(βchloroethyl)-aniline, N-methylanfline, N-methyl-2,5-dichloroaniline and N-ethylaniline.

Possible auxiliaries are all the virtually watersoluble organic solvents. These include, preferably, optionally halogenated hydrocarbons, such as benzene, xylenes, ethylbenzene, chlorobenzene, toluene, hexane, ligroin, cyclohexane and ethylene chloride. The reaction is carried out at temperatures between 0° C. and 100° C., preferably between 0° C. and 60° C.

The reaction is in general carried out under normal pressure.

The reaction is carried out in the acid range, preferably at a pH of the aqueous phase of between 4 and −1.

In carrying out the process according to the invention, approximately equimolar amounts of cyanuric chloride and a virtually water-insoluble arylamine are reacted in water with an acid pH value in the presence of a virtually water-insoluble organic solvent. A slight excess of the arylamine (1 to 2%) does no harm. The small amount of acid formed by introduction of cyanuric chloride into the water is in general sufficient for carrying out the process according to the invention. However, it is also furthermore possible for an additional acid, for example hydrochloric acid, to be dissolved in the aqueous phase. As a result of the hydrogen chloride formed in the reaction, the acid concentration in the aqueous phase increases greatly. This is no disadvantage for carrying out the process according to the invention. However, a procedure can also be followed in which the acid formed is neutralized down to a residue during the reaction time with a base, for example sodium hydroxide solution.

To avoid side reactions, the preferred procedure for the process according to the invention comprises adding the arylamine to the rest of the reaction mixture over a period of 10 to 60 minutes at between ±0° and +40° C. In spite of this relatively low temperature, a reaction time of only 1/2 to 1 hour is as a rule necessary. The reaction time required can be further shortened by increasing the reaction temperature, after the arylamine has been added, to a maximum of the boiling point of the reaction mixture. Finally, the product can be isolated by filtration and drying, if necessary after prior neutraliz ation of the reaction mixture or after distilling off the organic solvent.

The substances prepared according to the invention can be used as fungicides (compare, for example, U.S. Patent Specification No. 2,720,480).

The following examples illustrate the process according to the invention and once again show, in association with the comparison examples, the unexpected influence which the addition of a virtually water-insoluble organic solvent to the aqueous reaction mixture has.

PREPARATION EXAMPLES

Example 1

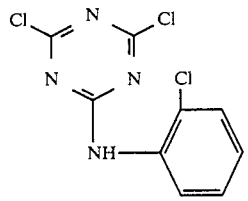

272.0 g of cyanuric chloride (content >99%), 1,000 ml of water and 275 ml of toluene are mixed at 5° C. The aqueous phase thereby assumes a pH value of 3.5. 188.2 g of o-chloroaniline are added in the course of 30 minutes without cooling or heating the mixture, whereupon the temperature rises to 30° C. A pH value of 7 is then established in the course of 1 hour by addition of 45% strength sodium hydroxide solution, whereupon the temperature rises up to 55° C. The mixture is then cooled to 20° C. in the course of 15 minutes. The product is filtered off, washed salt-free with water and dried at 60° C. in a waterpump vacuum. 396.5 g of 2-(2-chlorophenylamino)-4,6-dichloro-s-triazine are obtained with a melting point of 159° C. and a content of 98.9%, which corresponds to a yield of 97.5% (based on 99% pure cyanuric chloride).

The organic phase is removed from the filtrate by phase separation. It contains 4.2 g of dissolved product and can be recycled to the next batch, so that the yield is increased to 98.5%.

Example 2

272.0 g of cyanuric chloride, 730 ml of water and 552 ml of toluene are mixed in a stirred glass beaker at 5° C. 188.2 g of o-chloroaniline are added in the course of 15 minutes without cooling or heating the mixture. The mixture is subsequently stirred for 25 minutes and the temperature is thereby allowed to rise to 35° C. The mixture is then cooled to 20° C. in the course of 30 minutes. The product is filtered off, washed acid-free with water and dried at 60° C. under a waterpump vacuum. 333.6 g of 2-(2-chlorophenylamino)-4,6-dichloro-s-triazine with a content of 97.8% are obtained, which corresponds to a yield of 81.1%.

The organic phase is removed from the filtrate by phase separation. It contains 14.1 g of dissolved product and can be recycled to the next batch, so that the yield is increased to 84.6%.

Example 3

The procedure and batch are as for Example 2, but the mixture is subsequently stirred for 45 minutes and the temperature is thereby increased to 60° C. 367.0 g of product with a content of 98.1% are obtained, which corresponds to a yield of 89.5%.

The organic phase of the filtrate contains 10.6 g of dissolved product, so that when it is recycled, the yield is increased to 92.1%.

In the following comparison examples A and B, the conditions as described in Example 2 are maintained, except that only water is used in Example A and only toluene is used in Example B. In Example A, the content of product is 5% lower than in Example 2, with the same yield. In Example B, the content and yield are considerably lower than in Example 2.

Comparison Example A 272.0 g of cyanuric chloride and 1,282 ml of water are mixed at 5° C. 188.2 g of o-chloroaniline are added in the course of 15 minutes without cooling or heating the mixture. The mixture is subsequently stirred for 25 minutes and the temperature is thereby allowed to rise to 5° C. The mixture is then cooled to 20° C. in the course of 30 minutes. The product is filtered off, washed acidfree with water and dried at 60° C. under a waterpump vacuum. 372.8 g of product with a content of only 92.8% are obtained, which corresponds to a yield of 86.0%.

Comparison Example B 272.0 g of cyanuric chloride and 1,282 ml of toluene are mixed at 5° C. 188.2 g of o-chloroaniline are added in the course of 15 minutes without cooling or heating the mixture. The mixture is subsequently stirred for 25 minutes and the temperature is thereby allowed to rise to 35° C. The mixture is then cooled to 20° C. in the course of 30 minutes. The product is filtered off, washed acid-free with water and dried at 60° C. under a waterpump vacuum. 275.4 g of product with a content of only 57.8% are obtained, which corresponds to a yield of 39.6%.

The organic phase is removed from the filtrate by phase separation. It contains 56.0 g of dissolved product and can be recycled to the next batch. A total yield of only 53.5% results.

It will be understood that the specification and examples are illustrative but not limitative of the present invention and that other embodiments within the spirit and scope of the invention will suggest themselves to those skilled in the art.

What is claimed is:

1. In the preparation of a 2-arylamino-4,6-dichloro-s-triazine of the formula

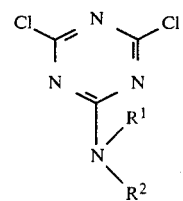

in which
$R^1$ is, a carbocyclic aryl radical which is optionally substituted by alkyl with 1 to 6 carbon atoms, nitro, cyano, alkoxy with 1 to 5 carbon atoms, halogen and/or halogenoalkyl with 1 to 5 carbon atoms and 1 to 5 halogen atoms, and
$R^2$ is hydrogen or alkyl, by reacting cyanuric chloride of the formula

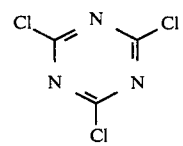

with a virtually water-insoluble arylamine of the formula

at a temperature between 0° and 100° C., the improvement which comprises effecting the reaction in water at an acid pH in the presence of a virtually water-insoluble organic solvent.

2. A process according to claim 1, in which
$R^1$ is a phenyl or naphthyl radical which is optionally substituted by alkyl with 1 to 6 carbon atoms, nitro, cyano, alkoxy with 1 to 5 carbon atoms, halogen and/or halogenoalkyl with 1 to 5 carbon atoms and 1 to 5 halogen atoms, and
$R^2$ is hydrogen or alkyl with 1 to 4 carbon atoms.

3. A process according to claim 1, in which
$R^1$ is a phenyl or naphthyl radical which is optionally mono-, di- or trisubstituted by alkyl with 1 to 4 carbon atoms, chlorine, nitro, cyano, alkoxy with 1 to 3 carbon atoms and/or halogenoalkyl with 1 to 3 carbon atoms and 1 to 5 chlorine and/or fluorine atoms, and
$R^2$ is hydrogen, methyl or ethyl.

4. A process according to claim 1, wherein the cyanuric chloride is reacted with a substantially equimolar amount of the arylamine.

5. A process according to claim 1, wherein the reaction is carried out at a temperature between 0° C. and 60° C.

6. A process according to claim 1, wherein the virtually water-insoluble organic solvent is an optionally chlorinated hydrocarbon.

7. A process according to claim 1, wherein the virtually water-insoluble organic solvent is toluene.

8. A process according to claim 1, wherein the pH of the aqueous phase is between 4 and −1.

* * * * *

UNITED STATES PATENT AND TRADEMARK OFFICE
CERTIFICATE OF CORRECTION

PATENT NO. : 4,683,308
DATED : July 28, 1987
INVENTOR(S) : Andreas Günther, et al.

It is certified that error appears in the above-identified patent and that said Letters Patent is hereby corrected as shown below:

| | |
|---|---|
| Col. 3, line 11 | Insert --1-- after "particular" |
| Col. 3, line 14 | Delete "eXample" and substitute --example-- |
| Coo. 3, line 30 | Delete "N-methylanfline" and substitute --N-methylaniline-- |
| Col. 5, line 29 | Delete "5°" and substitute --35°-- |

Signed and Sealed this

Sixteenth Day of August, 1988

Attest:

DONALD J. QUIGG

Attesting Officer

Commissioner of Patents and Trademarks